(12) United States Patent
Priesnitz et al.

(10) Patent No.: US 8,115,923 B2
(45) Date of Patent: Feb. 14, 2012

(54) MEASURING ARRANGEMENT FOR SPECTROSCOPIC EXAMINATION AND THROUGHPUT ACQUISITION OF A CROP FLOW

(75) Inventors: Rico Priesnitz, Blies-Ebersing (FR); Judith Stauder, Blies-Ebersing (FR)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 12/573,476

(22) Filed: Oct. 5, 2009

(65) Prior Publication Data
US 2010/0110428 A1 May 6, 2010

(30) Foreign Application Priority Data
Oct. 31, 2008 (DE) .................. 10 2008 043 377

(51) Int. Cl.
*G01J 3/28* (2006.01)
(52) U.S. Cl. ............................................. 356/326
(58) Field of Classification Search .............. 356/326
See application file for complete search history.

(56) References Cited

U.S. PATENT DOCUMENTS

| | | | |
|---|---|---|---|
| 5,092,819 A | 3/1992 | Schroeder et al. | |
| 5,751,421 A | 5/1998 | Wright et al. | |
| 6,791,683 B2 * | 9/2004 | Sjodin | 356/326 |

FOREIGN PATENT DOCUMENTS

| | | |
|---|---|---|
| DE | 19922867 A1 | 5/1999 |
| DE | 19922867 | 11/2000 |
| DE | 102004048103 A1 | 4/2006 |
| DE | 102008017671.0 | 10/2009 |
| EP | 0208025 A1 | 12/1985 |
| EP | 0208025 | 1/1987 |
| EP | 0843959 | 5/1998 |
| EP | 0940656 | 9/1999 |
| EP | 1305994 A1 | 10/2002 |
| EP | 1305994 | 5/2003 |

OTHER PUBLICATIONS

European Search Report, Sep. 15, 2011, 3 pgs.

* cited by examiner

*Primary Examiner* — Tarifur Chowdhury
*Assistant Examiner* — Abdullahi Nur

(57) ABSTRACT

A measuring arrangement for spectroscopic examination and throughput acquisition of a crop flow is provided, the arrangement having a spectrometer which comprises a light source, a window, a dispersive element and a detector, the light source is positioned to illuminate the crop flow during operation through the window, and positioned such that light reflected by the crop flow passes through the window and onto the dispersive element, which is positioned to deflect the reflected light onto the detector in different directions as a function of wavelength, a throughput-determining device cooperating with the crop flow, and a recording device for recording the measured values of the spectrometer and of the throughput determining device.

8 Claims, 4 Drawing Sheets

MEASURING ARRANGEMENT FOR SPECTROSCOPIC EXAMINATION AND THROUGHPUT ACQUISITION OF A CROP FLOW

BACKGROUND OF THE INVENTION

In the case of agricultural harvesting machines, there is a need to acquire the throughput of crop gathered from the agricultural field in which it is harvested, in order, for example, to document it for accounting purposes or for applications in precision agriculture. The throughput is usually measured by baffle plates which are arranged next to the crop flow and give way against the force of a spring owing to the impacting crop flow. The position of the baffle plate depends on the mass throughput (that is to say the crop mass flow per unit time), and is acquired by means of a sensor whose signal indicative of the throughput is preferably recorded together with a reference to the geographical location where the throughput measurement was made.

In the case of combine harvesters, such baffle plates are usually arranged at the outlet of the grain elevator, which conveys the grain upwards before being cleaned, inside a transitional housing from which it is brought into the grain tank by means of a screw conveyor (see EP 0 208 025 A1). EP 1 305 994 A1 proposes fitting a capacitive moisture sensor directly below the baffle plate.

In addition, various spectroscopic measuring devices have been described in the prior art which are used in agriculture in order to classify crop material, for example. DE19922867A1 describes a spectroscopic measuring device for agricultural harvesting machines which comprises a light source for the purpose of irradiating the crop with light. Light reflected by the sample is deflected in a spectrometer by a dispersive element, for example a grating or a prism, in different directions dependent on the wavelength. Detector elements receive the light, now assigned known wavelengths, the wavelengths of which light lie in the visible wavelength region or in the near infrared region. The output signals of the detector elements are fed to an evaluation device which uses the measured spectra to calculate specific parameters and proportions of materials contained in the sample. The measuring device is located directly next to the crop flow on a discharge device of the harvesting machine, while the volume of the crop is acquired by a sensor which determines the distance between adjacent rollers (sensor rollers) between which the crop passes.

U.S. Pat. No. 5,751,421A1 and U.S. Pat. No. 5,092,819A1 describe combine harvesters having a measuring device for spectroscopic examination or acquisition of materials contained in the crop, which are arranged at the outlet of the grain elevator and cooperate there with the crop.

In the case of the measuring devices according to U.S. Pat. No. 5,751,421A1 and U.S. Pat. No. 5,092,819A1, no continuous acquisition of the crop throughput is provided, and the measuring arrangements described in EP0208025A1 and EP1305994A1 permit no spectroscopic examination of the crop, the measuring arrangement in accordance with DE19922867A1 is subject to the disadvantage that there is a time offset between the acquisition of the throughput at the sensor and the spectroscopic examination of the same crop. The assignment of the spectra to the throughput measured values is therefore problematic and would require a precise acquisition of the current conveying speed through the harvesting machine in addition to a high computational outlay.

It is an object of this invention to provide a measuring arrangement for spectroscopic examination and throughput acquisition of a crop flow which enables in a simple way an improved temporal correlation between the acquisition of the throughput measured values and the recording of the spectra of the same crop.

This object is achieved in accordance with the invention by the teaching of claim 1 herein. Additional related features of the invention are set forth in the further patent claims which further develop the solution.

SUMMARY OF THE INVENTION

In accordance with a first aspect of the invention, a measuring arrangement comprises a spectrometer for determining the materials contained in the crop flow, which spectrometer is equipped with a light source which illuminates the crop flow through a window during the measurement operation. The spectrometer further comprises a dispersive element, for example a prism, a grating or a slit, which reflects in a spectrally decomposed fashion, that is to say in different directions as a function of the respective wavelength, light reflected by the crop flow, originating from the light source and re-entering through the window. A detector having a multiplicity of photosensitive elements, for example photodiodes or CCDs, receives the dispersed light. Since the position of the respective element of the detector can be assigned to a wavelength, the spectrometer supplies spectra of the sample which, with the aid of calibration data, can be used in a suitable electronic evaluation device to determine the materials contained in the crop flow. Moreover, the measuring device comprises a throughput-determining device which cooperates, preferably mechanically, with the crop in order to determine the respective (volume and/or mass) throughput per unit time. The throughput-determining device and the spectrometer are connected to a recording device which records or stores the measured values both of the throughput determining device and of the spectrometer during operation. The throughput determining device and the spectrometer are arranged in close vicinity of one another.

In this way, the measured values of the throughput determining device and of the spectrometer can be assigned with adequate accuracy to the same crop. The temporal correlation of the two measured values is therefore substantially improved. The measured values can be recorded for accounting purposes, for example to determine the commercial value of the crop with the aid of the quantity and the content of specific materials contained, such as proteins, or for the purposes of precision agriculture, in particular in order to be able to carry out in a fashion specific to location subsequent fertilizing with the aid of the yield of the crop and of the materials contained therein. Moreover, the measured values can be used for the automatic setting of components of the harvesting machine, since, for example, the spectra of the spectrometer can be used to detect possible contaminations, and this in turn can be used to improve the setting of the cleaning of a combine harvester. For example, contaminants may absorb different spectra, proportionately, than the crop absorbs and thus has a different spectral signature. In this case, the evaluation device can be configured to determine a value indicative of the amount of contaminants in the crop stream, and provide this to an electronic control unit that will in turn set components of the harvesting machine to reduce the amount of contaminants.

In one embodiment of the invention, the throughput determining device comprises a movably supported, pre-stressed baffle plate against which the crop flow bounces. The deflection of the baffle plate against the pre-stressing provided as a rule by means of a spring depends on the mass throughput and is acquired by means of a position sensor. However, it would also be conceivable to use the throughput-determining device to acquire the volume throughput for example by means of a plate which can be moved transverse to the flow direction, or a roller which is pre-stressed against the crop flow and is moved by it, while the spectrometer cooperates through a window in the plate with the crop or is arranged inside the roller and cooperates with the crop through an annular window in the roller. The throughput determining device could also determine the volume of the crop optically (instead of mechanically). For example, see DE102008017671A1 and the references quoted there.

The spectrometer may be arranged directly upstream or downstream of the throughput determining device with reference to the flow direction of the crop flow, or its window may be arranged inside an opening in the baffle plate of the throughput determining device. In the latter case, the entire spectrometer can move together with the baffle plate when the baffle plate is deflected by the crop, or when the actual spectrometer (with the exception of the window) is stationary, and only the window moves with the baffle plate. The actual spectrometer except for the window—that is to say the light source, the dispersive element and the detector—can also be located inside a common housing with the position sensor of the throughput determining device.

The inventive measuring arrangement can be used on any desired harvesting machine, such as self-propelled, attached or towed balers, forage harvesters or combine harvesters. A preferred fitting position in the case of combine harvesters is at the outlet of an elevator for clean grain inside a transitional housing.

BRIEF DESCRIPTION OF THE DRAWINGS

Five exemplary embodiments of the invention that are described in more detail below are illustrated in the drawings, in which.

DETAILED DESCRIPTION OF THE PREFERRED EMBODIMENTS

Figure 1:
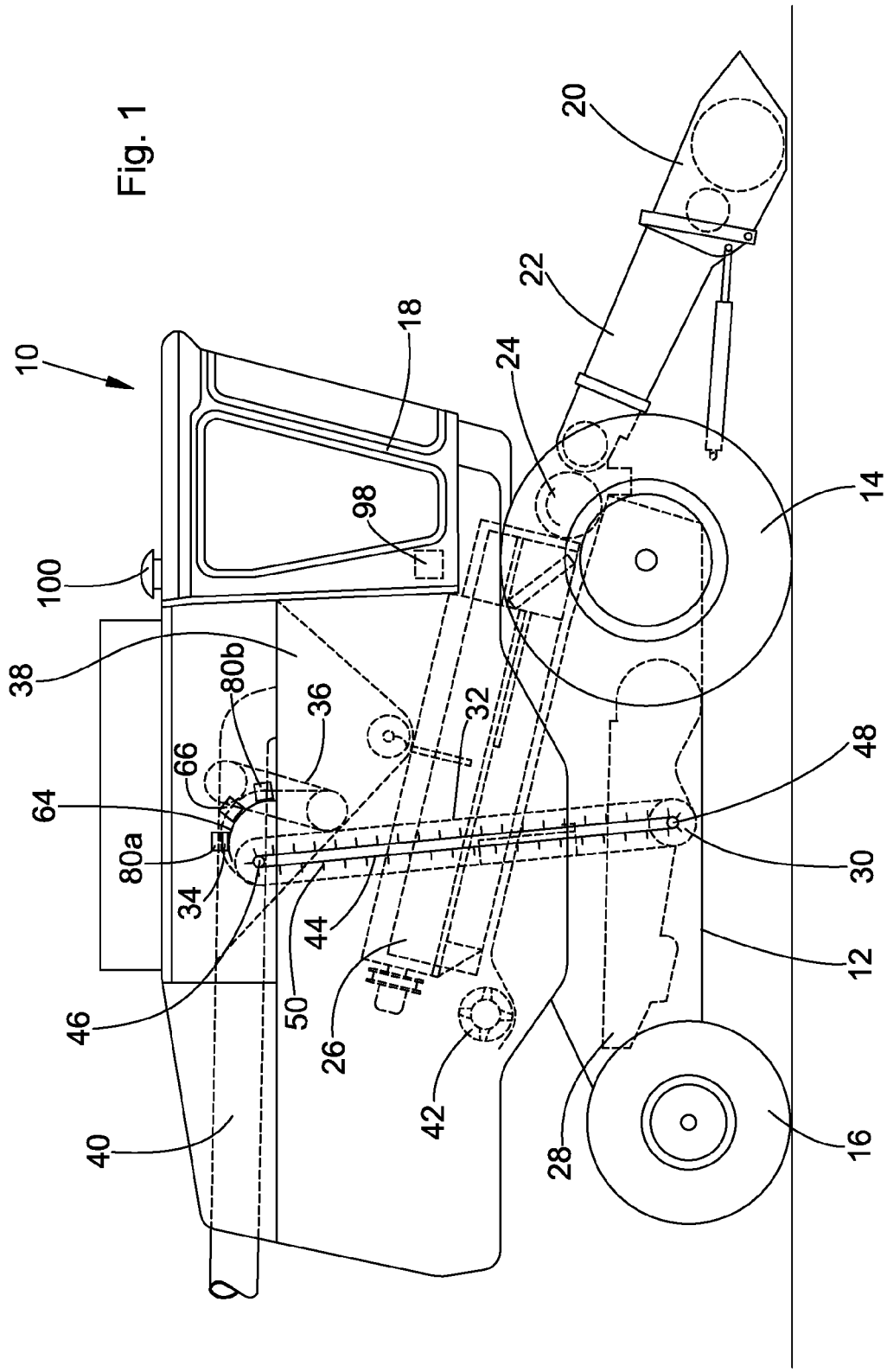
FIG. 1 shows a diagrammatic side view of a harvesting machine having an inventive measuring arrangement for spectroscopic examination and for determining the throughput of a crop flow, two embodiments being provided with regard to the fitting of the spectrometer.

FIG. 1 shows a self-propelled agricultural harvesting machine 10 in the form of a combine harvester having a frame 12 on both sides of which there are fitted front wheels 14 which make contact with the ground and serve to drive the harvesting machine 10 forwards in a forward direction (i.e. to the right in FIG. 1), as well as rear, steerable wheels 16. The operation of the harvesting machine 10 is controlled from the operator cabin 18. In the harvesting mode, a cutting unit or harvesting head 20 is used to harvest crop containing grain and to feed it to an inclined conveyor or feederhouse 22. The harvested material is fed by the inclined conveyor 22 to a feeder drum 24 which feeds the crop to an axial crop processing device 26.

Directional information expressed herein, such as "in front", "forward", "behind", "at the rear", etc., relates to the direction of travel the harvesting machine 10.

The crop processing device 26 comprises a rotor housing and a rotor arranged therein and on which material processing elements are fastened. Instead of an axial crop processing unit 26, it is also possible to use a tangential threshing drum followed by an axial separating device or straw shaker. Grain and chaff, which fall through a threshing basket and a separating grate, are fed to a cleaning system 28 having a fan and oscillating sifters. The cleaning system 28 removes the chaff and leads the clean grain via a screw conveyor 30 to an elevator 32 for clean grain, which conveys the clean grain into a transitional housing 34 from which it is conveyed into a grain tank 38 by means of a further screw conveyor 36. The clean grain in the grain tank 38 is discharged by a discharge screw conveyor 40 onto a grain wagon, trailer or lorry. Threshed straw which has left the crop processing device 26 is ejected through an outlet from the crop processing device 26 and fed to an ejection drum 42 which ejects the straw rearwards or feeds it to a straw chopper (not shown).

Figure 2:
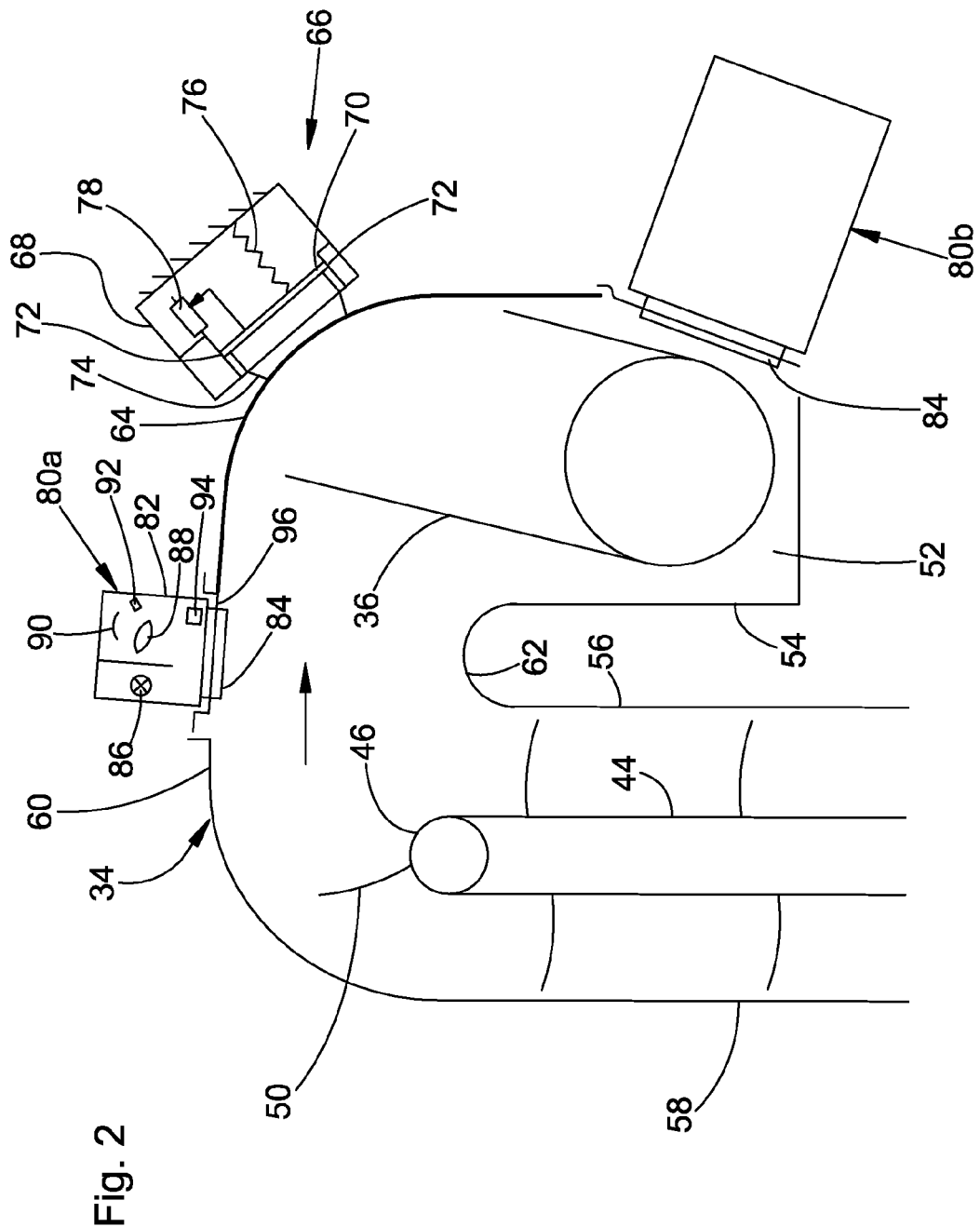
FIG. 2 shows an enlarged side view of the outlet region of the grain elevator of the harvesting machine from FIG. 1.

FIG. 2 shows the transitional housing 34 in an enlarged illustration. The elevator 32 is designed as a paddle conveyor and comprises one or more chains 44 which circulate around an upper deflection wheel 46 and a lower deflection wheel 48 of which one is driven. The chain 44 supports a plurality of blade-shaped paddles 50 which deliver approximately horizontally above the upper deflection wheel 46 the grain conveyed upwards thereto. The transitional housing 34 comprises a trough 52 in which the inlet of the further screw conveyor 36 is located, and which is bounded by a wall 54 that extends downward and toward the elevator 32. The lateral part of the wall 54 is connected by a roof-shaped portion 62 to a rear wall 56 of a housing of the elevator 32 which is enclosed at the front by a front wall 58. The front wall 58 merges in a curved fashion at its top side into a cover 60 of the transitional housing 34. On the side situated opposite the outlet of the elevator 32, the transitional housing 34 is bounded upwards and to the front by a concavely curved baffle plate 64 of a throughput-determining device 66 against which the grain ejected by the elevator 32 bounces.

The throughput-determining device 66 furthermore comprises a housing 68 which is positioned on the outside of the baffle plate 64 and of the transitional housing 34 and is rigidly connected to the frame 12. A plate 70 is displaceably supported in the housing 68 by guides 72 in a direction running obliquely upwards and forwards. The plate 70 is rigidly connected by a tube 74 to the baffle plate 64 and can move with the baffle plate 64 and the tube 74 in relation to the housing 68. A spring 76 pre-stresses the plate 70 downwards and to the rear such that the plate 70 is moved upwards and forwards against the force of the spring 76 by grain striking the baffle plate 64. A position sensor 78 in the form of a potentiometer acquires the position of the plate 70 and therefore the position of the baffle plate 64 such that the output signal of the position sensor 78 is a measure of the mass throughput of the crop flow delivered by the elevator 32.

Spectrometers 80a, 80b are illustrated in FIGS. 1 and 2 in two different positions. As a rule, only one of the spectrometers 80a or 80b is installed. The two illustrated spectrometers 80a, 80b serve to demonstrate the two positioning options. The spectrometers 80a, 80b are of an identical design which is discussed below with the aid of the spectrometer 80a. The spectrometer 80a comprises a housing 82 with an opening in which there is arranged a window 84 whose pane preferably consists of sapphire glass or another adequately wear resistant material which is sufficiently transparent in the wavelength region to be examined. Located inside the housing 82 is a light source 86 which shines a broadband, so-called white light which covers in near infrared region, through the window 84, and onto the crop flow delivered by the elevator 32.

Light reflected by the crop flow re-enters the housing 82 back through the window 84 and is guided by a lens system 88 onto a dispersive element 90 in the form of a concave mirror. The concave mirror has a grating structure provided on its underside that deflects the light in various directions as a function of the wavelength of the light. This deflected light then reaches a detector 92 that has a row of photosensitive elements. Each of these photosensitive elements outputs a signal dependent on the intensity of the light received by that element. An evaluation device 94 connected to the detector 92 evaluates the output signals of the detector 92 and supplies spectra and/or information derived therefrom, for example fractions of materials contained in the crop flow. Suitable spectrometers are described in DE19922867A1, and in DE102004048103A1, the disclosures of which are also incorporated by reference into the present application in their entirety for any purpose.

The spectrometer 80a is arranged above the cover 60 of the transitional housing 34, the window 84 being located inside an opening in a ramp 96 which is arranged directly upstream of the baffle plate 64. The ramp 96 serves the purpose of directing the crop flow delivered by the elevator 32 onto the baffle plate 64 and, in particular, of preventing grain at the front edge, with reference to the crop flow, of the baffle plate 64 from undesirably reaching the outside thereof. Owing to a setting of the ramp 96 and of the window 84 about a relatively small angle, which can be between 3 and 5°, for example, the mass flow of the crop gives rise to a self-cleaning function of the glazing or pane of the window 84 of the spectrometer 80a. The effect of this is to counteract contamination and/or accumulation of deposits of crop residues or other dirt particles on the pane of the window 84.

By contrast, the spectrometer 80b is arranged at that end of the baffle plate 64 which lies downstream, the window 84 extending obliquely downwards and rearwards towards the middle of the trough 52. The windows 84 of the two spectrometers 80a, 80b are bathed by the crop flow such that possible contaminants are entrained and do not adhere to the windows 84.

Via a bus system or an assigned cable or via radio or optically, the evaluation device 94 of the spectrometer 80a or 80b and the position sensor 78 of the throughput-determining device 66 are connected to a recording device 98 which is located in the operator cabin 18, compare FIG. 1. The recording device 98 is furthermore connected to a position-determining device 100 in the form of an antenna, and to receiving devices for receiving and processing signals from a satellite-based position-determining system, for example GPS or Glonass or Eureka. The signals of the evaluation device 94 of the spectrometer 80a or 80b and of the position sensor 78 of the throughput determining device 66 are therefore recorded by the recording device 98 in geo-referenced fashion, in order to be able to use them later for accounting purposes or for use in precision agriculture. However, these signals can be used for automatically setting components of the harvesting machine 10, for example to set the fan speed and sifter aperture of the cleaning system 28, or the speed of the axial crop-processing device 26. The fitting of the spectrometer(s) 80a and/or 80b and of the throughput-determining device 66 directly next to one another has the advantage that in each case measured values of the same crop are acquired, that is to say that the temporal correlation of the measured values is very good.

Figure 3:
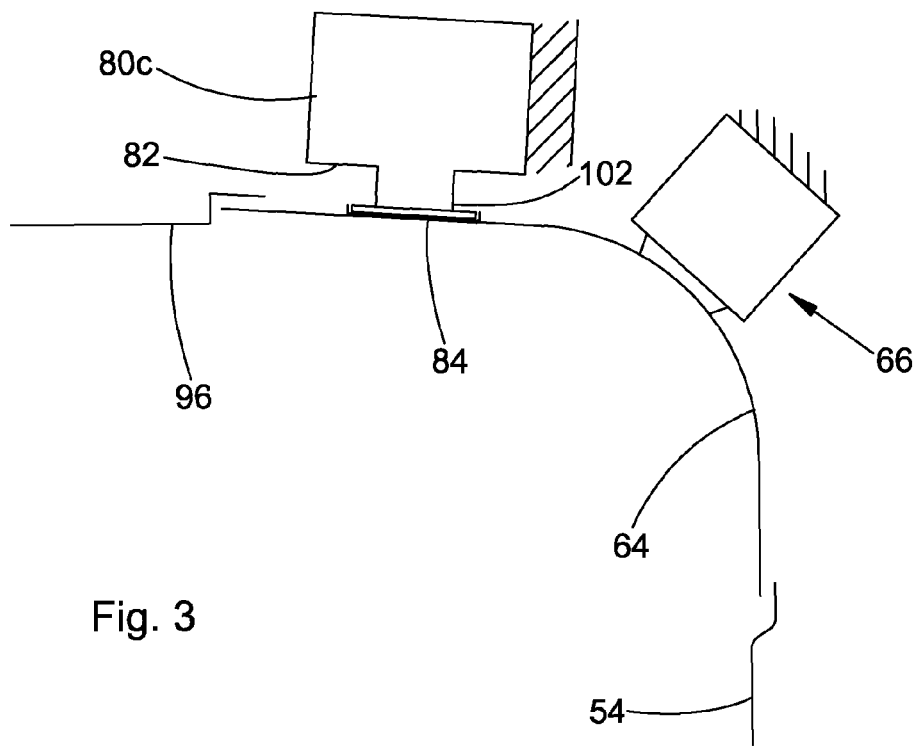
FIG. 3 shows an enlarged side view of the outlet region of the grain elevator of the harvesting machine from FIG. 1 with a third embodiment of an inventive measuring arrangement.

Reference is now made to FIG. 3, in which there is illustrated a further option for fitting a spectrometer 80c. Elements similar to the embodiment according to FIGS. 1 and 2 are provided with the same reference symbols. The housing 82 of the spectrometer 80c is here rigidly connected to the frame 12 of the harvesting machine 10, while the window 84 is recessed rigidly into the upper region of the baffle plate 64, which still extends approximately horizontally. Since the baffle plate 64 moves in relation to the frame 12 in the harvesting mode, a movement is also provided between a lower connecting piece 102 of the housing 82 and the window 84 through which the light passes from the housing 82 to the window 84, and vice versa. The connecting piece 102 can also be partially or completely of flexible design, for example designed as a bellows, and be rigidly connected to the edge of the window 84.

Figure 4:
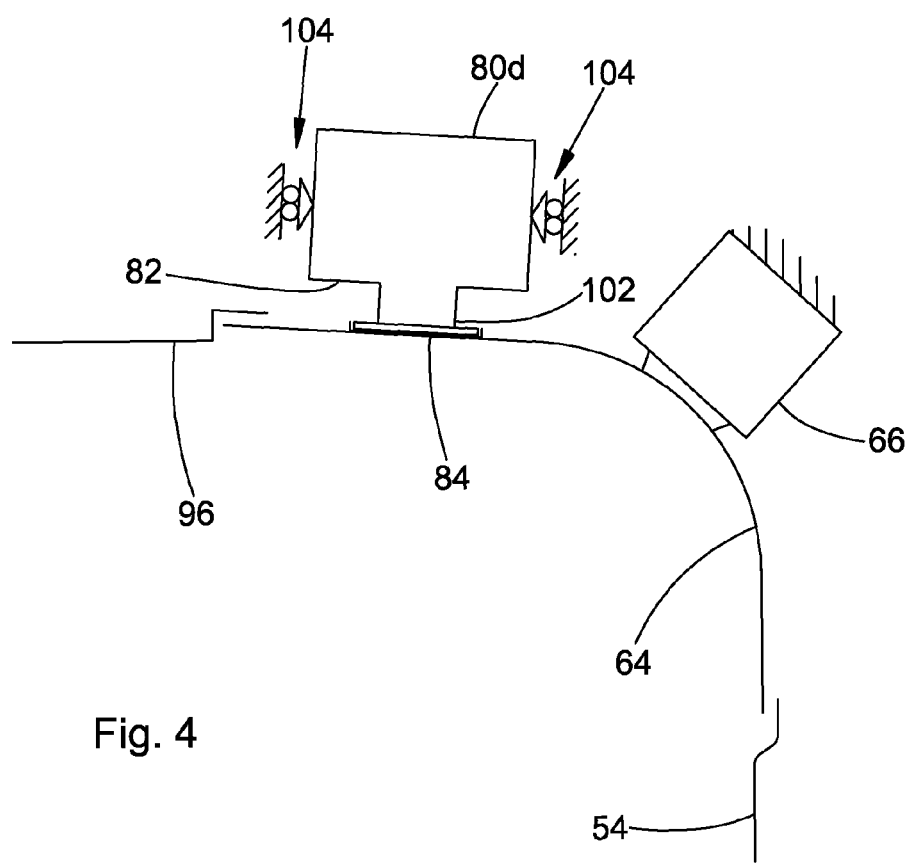
FIG. 4 shows an enlarged side view of the outlet region of the grain elevator of the harvesting machine from FIG. 1 with a fourth embodiment of an inventive measuring arrangement.

The measuring arrangement illustrated in FIG. 4 corresponds substantially to the embodiment according to FIG. 3, but the housing 82 of the spectrometer 80d is rigidly connected via the connecting piece 102 to the edge of the window 84 and therefore moves together with the baffle plate 64. The housing 82 of the spectrometer 80d is, furthermore, supported by bearings 104 on the frame 12 of the harvesting machine 10, and said bearings enable the housing 82 to track the movement of the baffle plate 64 by enabling a vertical movement of the housing 82 by means of ball bearings and a swivelling movement of the housing by prism bearings.

Figure 5:
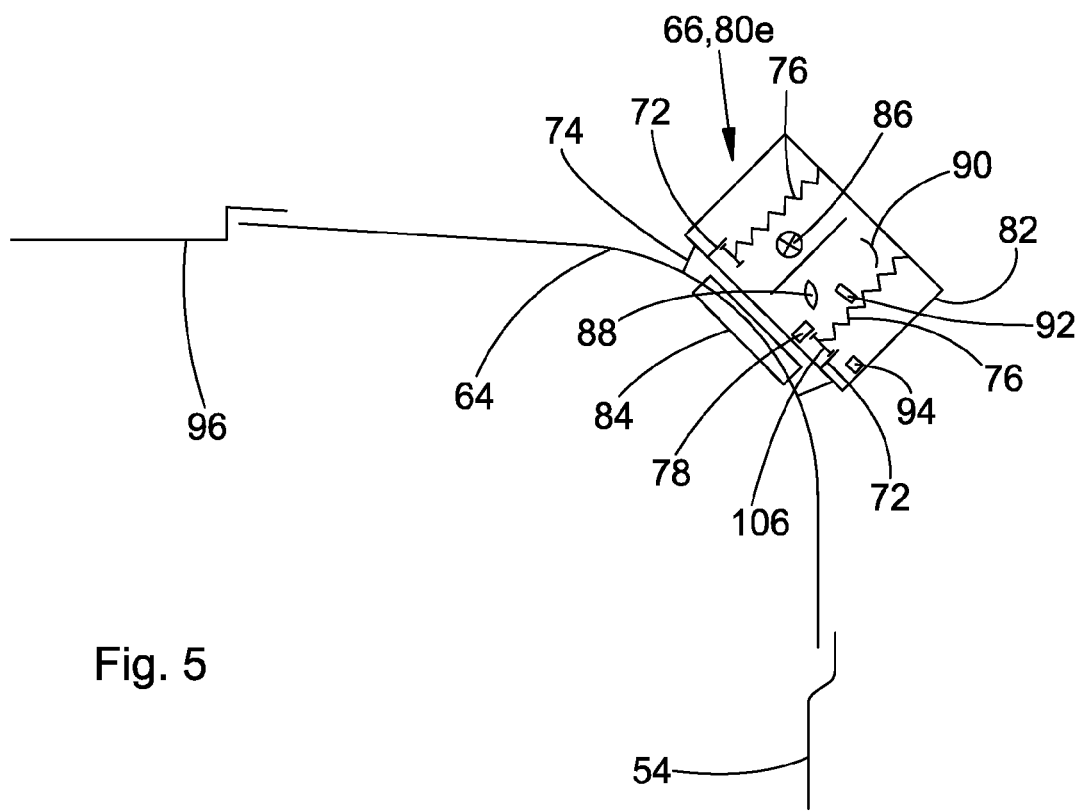
FIG. 5 shows an enlarged side view of the outlet region of the grain elevator of the harvesting machine from FIG. 1 with a fifth embodiment of an inventive measuring arrangement.

Illustrated in FIG. 5 is a fifth embodiment, in the case of which elements corresponding to the preceding embodiments have been provided with the same reference symbols. The essential difference from the preceding embodiments resides in the fact that the light source, the dispersive element and the detector of the spectrometer 80e, on the one hand, and the position sensor 72 and the spring 76 of the throughput-determining device 66, on the other hand, are arranged inside a common housing 82 which is fastened in a stationary fashion on the frame 12 of the harvesting machine 10. The window 84 is located in the region below the maximum curvature of the baffle plate 64 and is mounted fixedly on the baffle plate 64 in a corresponding segment of the same. The baffle plate 64 is connected via a tube 74 to a ring 106 which is prestressed by springs 76 in the direction of the crop flow and is displaceably supported in guides 72. The position of the ring 106 in its direction of displacement is acquired by means of the position sensor 72, in a way similar to the embodiment in accordance with FIG. 2. Also accommodated in the housing 82 are the light source 86, the lens system 88, the dispersive element 90 and the detector 92 of the spectrometer 80e, as well as its evaluation device 94. The operating principles of the measuring arrangements according to FIGS. 3 to 5 correspond to those of the measuring arrangement according to FIGS. 1 and 2.

The invention claimed is:
1. A measuring arrangement for spectroscopic examination and throughput acquisition of a crop flow, comprising:
a spectrometer (80a, 80b, 80c, 80d, 80e) which comprises a light source (86), a window (84), a dispersive element (90) and a detector (92), the light source (86) is positioned to illuminate the crop flow during operation through the window (84), and positioned such that light reflected by the crop flow coming through the window (84) falls onto the dispersive element (90), which is positioned to deflect the light onto the detector (92) in different directions as a function of wavelength;

a throughput-determining device (66) cooperating with the crop flow; and a recording device (98) for recording the measured values of the spectrometer (80a, 80b, 80c, 80d, 80e) and of the throughput determining device (66);

in which the throughput determining device (66) and the spectrometer (80a, 80b, 80c, 80d, 80e) are arranged in the direct spatial vicinity of one another.

2. The measuring arrangement according to claim 1, in which the throughput determining device (66) comprises a movable, pre-stressed baffle plate (64) against which the crop flow bounces during operation and whose position can be acquired by means of a position sensor (72).

3. The measuring arrangement according to claim 1, in which with reference to the crop flow the spectrometer (80a, 80b, 80c, 80d, 80e) is arranged directly upstream or directly downstream of the throughput determining device (66) or inside an opening in the throughput-determining device (66).

4. The measuring arrangement according to claim 3, in which the window (84) of the spectrometer (80c, 80d, 80e) is fixed inside the baffle plate (64), and in that the light source (86), the dispersive element (90) and the detector (92) are connected in a stationary fashion and therefore movably relative to the baffle plate (64), or rigidly to the baffle plate (64).

5. The measuring arrangement according to claim 1, in which the light source (86), the dispersive element (90) and the detector (92) of the spectrometer (80e) are arranged inside a housing (82) in which the position sensor (72) of the throughput-determining device (66) is also located.

6. The measuring arrangement according to claim 1 in which the recording device (98) is connected to a position-determining device (100) and can be operated to record the measured values of the spectrometer (80a, 80b, 80c, 80d, 80e) and of the throughput-determining device (66) with reference to location.

7. A harvesting machine (10) having a measuring arrangement according to claim 1.

8. A harvesting machine comprising a combine-harvester with an elevator (32), a transitional housing (34), a measuring arrangement for spectroscopic examination and throughput acquisition of a crop flow, further comprising a spectrometer (80a, 80b, 80c, 80d, 80e) which comprises a light source (86), a window (84), a dispersive element (90) and a detector (92), the light source (86) illuminating the crop flow during operation through the window (84), and light reflected by the crop flow coming through the window (84) onto the dispersive element (90), which deflects it onto the detector (92) in different directions as a function of wavelength; a throughput-determining device (66) cooperating with the crop flow; and a recording device (98) for recording the measured values of the spectrometer (80a, 80b, 80c, 80d, 80e) and of the throughput determining device (66), said elevator being configured to transport clean grain during harvesting operations from a cleaning system (28) into the transitional housing (34) from which the grain is conveyed into a grain tank (38), in which the measuring arrangement is positioned in the transitional housing (34) opposite the outlet of the grain elevator (32).

* * * * *